United States Patent
Sobol et al.

(10) Patent No.: US 12,193,741 B2
(45) Date of Patent: Jan. 14, 2025

(54) USING A MOBILE DEVICE TO FACILITATE MONITORING RETINAL DISEASES OCT METHODS AND SYSTEMS

(71) Applicant: CASE WESTERN RESERVE UNIVERSITY, Cleveland, OH (US)

(72) Inventors: Warren M. Sobol, Beachwood, OH (US); Alan Dogan, Hillsborough, NJ (US); Ellis Saupe, Strongsville, OH (US)

(73) Assignees: CASE WESTERN RESERVE UNIVERSITY, Cleveland, OH (US); UNIVERSITY HOSPITALS CLEVELAND MEDICAL CENTER, Cleveland, OH (US); THE UNITED STATES GOVERNMENT AS REPRESENTED BY THE DEPARTMENT OF VETERAN AFFAIRS, Washington, DC (US)

( * ) Notice: Subject to any disclaimer, the term of this patent is extended or adjusted under 35 U.S.C. 154(b) by 677 days.

(21) Appl. No.: 17/338,262

(22) Filed: Jun. 3, 2021

(65) Prior Publication Data
US 2021/0378505 A1 Dec. 9, 2021

Related U.S. Application Data

(60) Provisional application No. 63/034,739, filed on Jun. 4, 2020.

(51) Int. Cl.
*A61B 5/00* (2006.01)
*A61B 3/10* (2006.01)
(Continued)

(52) U.S. Cl.
CPC ............ *A61B 3/102* (2013.01); *A61B 5/0013* (2013.01); *H04W 76/14* (2018.02); *H04W 76/30* (2018.02); *G06F 3/0484* (2013.01); *H04W 88/06* (2013.01)

(58) Field of Classification Search
CPC ..... A61B 3/102; A61B 5/0013; A61B 5/0066; A61B 3/12; A61B 3/0016; H04W 76/14; H04W 76/30; H04W 88/06; G06F 3/0484
See application file for complete search history.

(56) References Cited

U.S. PATENT DOCUMENTS 7,275,830 B2   10/2007 Alster et al.
8,134,366 B2   3/2012 Quaet-Faslem et al.
(Continued)

OTHER PUBLICATIONS

Hari Nanakumar and Shailesh Srivastava; "Low Cost Open-Source OCT Using Undergraduate Lab Components"; IntechOpen; Aug. 24, 2020; 15 pgs.

(Continued)

*Primary Examiner* — Juan M Guillermety
(74) *Attorney, Agent, or Firm* — Tarolli, Sundheim, Covell & Tummino LLP

(57) ABSTRACT

An example method includes establishing a wireless link between a mobile device and an optical coherence tomography (OCT) test system, which includes a wireless interface. The method also includes executing an application on the mobile device to present a graphical user interface on a display of the mobile device. The method also includes sending instructions from the mobile device through the wireless link to activate the OCT test system to record OCT measurements for an OCT scan of at least one eye. The method also includes receiving OCT test data at the mobile device from the OCT test system through the wireless link. The OCT test data can represent the OCT measurements (Continued)

recorded by the OCT test system for the OCT scan of the at least one eye.

23 Claims, 6 Drawing Sheets

(51) Int. Cl.
*G06F 3/0484* (2022.01)
*H04W 76/14* (2018.01)
*H04W 76/30* (2018.01)
*H04W 88/06* (2009.01)

(56) References Cited

U.S. PATENT DOCUMENTS

| | | | |
|---|---|---|---|
| 8,195,937 | B2 | 6/2012 | Wise et al. |
| 8,764,655 | B2 | 7/2014 | Yoo |
| 9,492,079 | B2 | 11/2016 | Walsh et al. |
| 10,165,941 | B2 | 1/2019 | Walsh et al. |
| 10,595,722 | B1 | 3/2020 | Pascal et al. |
| 10,610,096 | B2* | 4/2020 | Scheibler ............ A61B 3/10 |
| 2012/0184846 | A1* | 7/2012 | Izatt ............ A61B 5/0073 356/479 |
| 2018/0146499 | A1* | 5/2018 | Jun ............ A61B 5/0015 |
| 2018/0271363 | A1 | 9/2018 | Scheibler et al. |
| 2019/0110753 | A1 | 4/2019 | Zhang et al. |
| 2019/0117074 | A1* | 4/2019 | Chen ............ A61B 5/00 |
| 2019/0125190 | A1* | 5/2019 | Boppart ............ A61B 5/415 |
| 2019/0254518 | A1 | 8/2019 | Rafaeli et al. |
| 2019/0392932 | A1* | 12/2019 | Wallace ............ A61B 5/055 |
| 2020/0077883 | A1* | 3/2020 | Ehlers ............ A61B 5/004 |
| 2020/0245867 | A1 | 8/2020 | Pascal et al. |
| 2020/0394789 | A1* | 12/2020 | Freund ............ A61B 3/102 |
| 2023/0020468 | A1* | 1/2023 | Kubota ............ A61B 3/12 |

OTHER PUBLICATIONS

Sanghoon Kim, Michael Crose, Will J. Eldridge, Brian Cox, William J. Brown, and Adam Wax, "Design and implementation of a low-cost, portable OCT system," Biomed. Opt. Express 9, Mar. 1, 2018; 12 pgs.

Song, G., Chu, K. K., Kim, S., Crose, M., Cox, B., Jelly, E. T., . . . Wax, A. (2019). First Clinical Application of Low-Cost OCT. Translational Vision Science & Technology, 8(3), 61. doi:10.1167/tvst.8.3.61.

Wittenborn JS, Clemons T, Regillo C, Rayess N, Liffmann Kruger D, Rein D. Economic Evaluation of a Home-Based Age-Related Macular Degeneration Monitoring System. JAMA Ophthalmol. 2017;135(5):452-459. doi: 10.1001/amaophthalmol.2017.0255.

Glenn J. Jaffe, MD and Joseph Caprioli, MD; "Optical Coherence Tomography to Detect and Manage Retinal Disease and Glaucoma"; Elsevier, American Journal of Ophthalmology; vol. 137, Issue 1, Jan. 2004, pp. 156-169; https://doi.org/10.1016/S0002-9394(03)00792-X.

Tauan de Oliveira, et al.; "Oct Angiography Compared to Fluorescein Angiography, Indocyanine Green Angiography and Optical Coherence Tomography in the Detection of Choroidal Neovascularization in Pigment Epithelial Detachment"; Acta Ophthalmol. 2019: 97: e1006-31012; 2019 Acta Ophthalmologica Scandinavica Foundation. Published by John Wiley & Sons Ltd; doi: 10.1111/aos.14117.

Talisa E de Carlo, et al.; "A Review of Optical Coherence Tomography Angiography (OCTA)"; International Journal of Retina and Vitreous; BioMed Central; (2015) 1:5; doi:10.1186/s40942-015-0005-8; 15 pgs.

Salomon Y. Cohen, MD, PhD and Sarah Mrejen MD; Imaging of Exudative Age-Related Macular Degeneration: Toward a Shift in the Diagnostic Paradigm?; Retina: Sep. 2017—vol. 37—Issue 9—p. 1625-1629 doi: 10.1097/IAE.0000000000001695.

* cited by examiner

USING A MOBILE DEVICE TO FACILITATE MONITORING RETINAL DISEASES OCT METHODS AND SYSTEMS

CROSS-REFERENCE TO RELATED APPLICATION

This application claims the benefit of priority to U.S. provisional patent application No. 63/034,739, which was filed Jun. 4, 2020, and is incorporated herein by reference in its entirety.

TECHNICAL FIELD

This disclosure relates to systems, devices and methods for monitoring retinal diseases using optical coherence tomography (OCT).

BACKGROUND

The most common retinal diseases, which include age-related macular disease (AMD), cataracts, diabetic retinopathy (DR) and glaucoma, affect over 70 million people in the United States. Many patients affected by retinal conditions are unaware of their diagnosis. When left undiagnosed and untreated, retinal diseases progress rapidly and can result in severe and irreversible vision loss. The current standard for retinal disease detection is using optical coherence tomography (OCT), which is a non-invasive imaging test that uses light waves to take high resolution images of the retina. Ophthalmologists take regular OCT scans of patients to monitor retinal changes and determine when treatment is needed. However, even though OCT exists, there are still millions of patients that are not diagnosed or experience preventable vision loss. This is because most OCT systems are only available for clinical use in hospitals and the offices of eye care professionals. Aside from the logistics of scheduling eye care appointments, it is difficult for patients to find transportation to a facility where routine examination and use OCT equipment is available. Therefore, many people go without proper eye care and do not get OCT scans until the onset of the disease is advanced. Additionally, once diagnosed with a retinal disease, there are often insufficient routine office visits available to enable the health care providers to adequately track and treat retinal disease.

Once a diagnosis of retinal disease is made, and known to the patient and their eye care provider, staging of the disease process and monitoring treatment response becomes important in treatment decisions. Individualized counseling and assessment of treatment is most commonly performed based on OCT findings, making frequent scans (and many trips back to a physician's office) a substantial and necessary burden on the patient and family. The specter of potential visual loss without frequent follow up OCT scans weighs heavily on these patients.

Finally, it has become a well-accepted paradigm among eye care professionals that various OCT findings are predictive of future progression of retinal diseases. Therefore easier access for patients to obtain OCT evaluation with remote interpretation of scan results would seem to be an imperative.

SUMMARY

Figure 1:
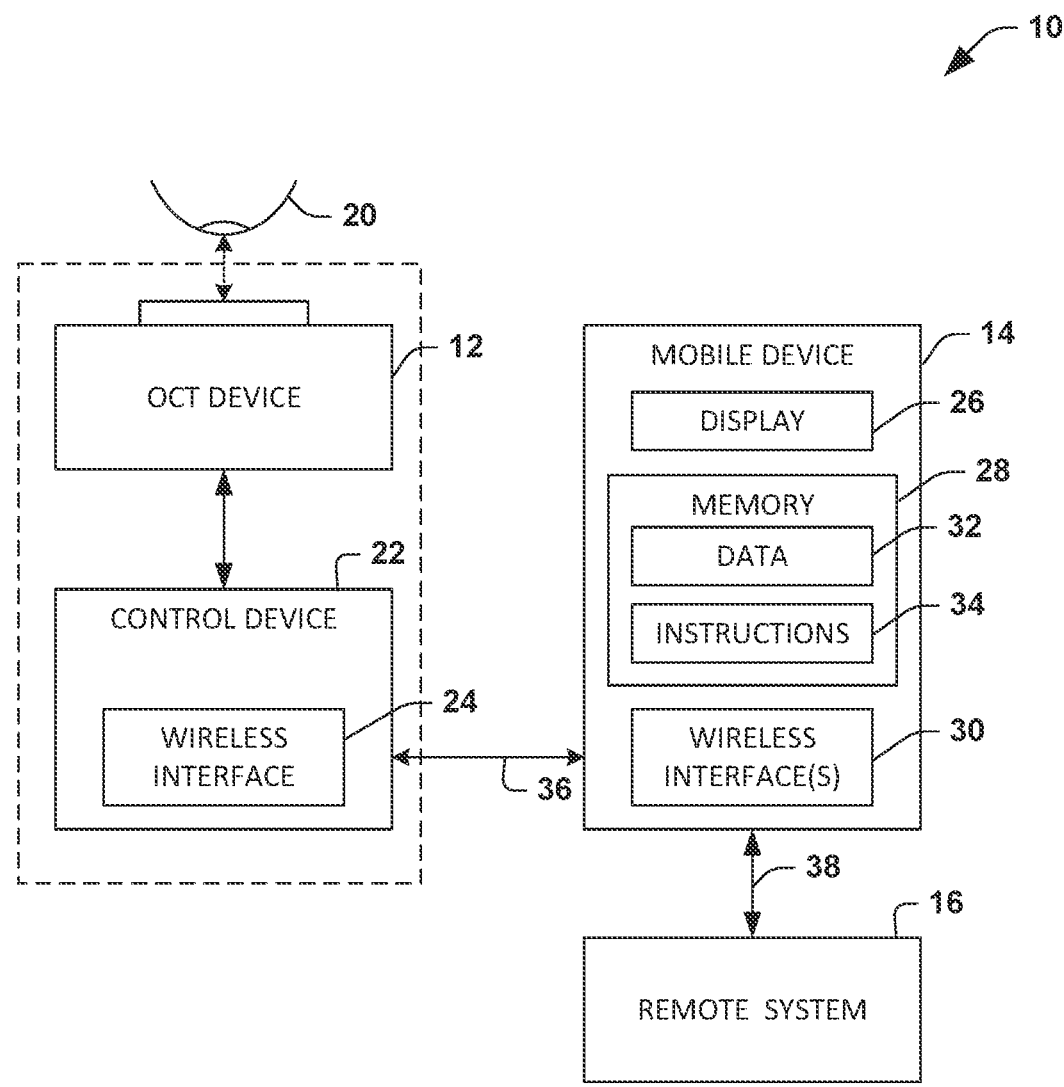
FIG. 1 is a block diagram of an example retinal disease monitoring system.

An example method includes establishing a wireless link between a mobile device and an optical coherence tomography (OCT) test system, which includes a wireless interface. The method also includes executing an application on the mobile device to present a graphical user interface on a display of the mobile device. The method also includes sending instructions from the mobile device through the wireless link to activate the OCT test system to record OCT measurements for an OCT scan of at least one eye. The method also includes receiving OCT test data at the mobile device from the OCT test system through the wireless link. The OCT test data can represent the OCT measurements recorded by the OCT test system for the OCT scan of the at least one eye. The method also includes terminating the wireless link to disconnect the mobile device from the OCT test device, and sending the received OCT test data from the mobile device to a remote system. In an example, the method can be a computer implemented method stored in one or more non-transitory machine readable media, and which is executable by a processor.

Another described example relates to a system for monitoring retinal disease. The system includes a retinal disease testing system and a mobile device. The retinal disease testing system includes an optical coherence tomography (OCT) device configured to record OCT image data in response to an OCT scan, a wireless interface and a control device configured to control the OCT device and the wireless interface. The mobile device includes a wireless interface, a display, and non-transitory memory that includes instructions configured to connect the wireless interface of the mobile device with the wireless interface of the testing system through a wireless link. The instructions are also configured to provide a graphical user interface (GUI) on the display of the mobile device, in which the GUI includes graphical control element. The instructions are further configured to send activation instructions from the mobile device through the wireless link to the OCT test device responsive to activating the graphical control element. The control device of the testing system is configured to control the OCT test device to record OCT measurements of the at least one eye responsive to the activation instructions and provide OCT test data. The mobile device further is configured to receive the OCT test data through the wireless link and store the received OCT test data in the memory of the mobile device. The stored OCT test data can represent the OCT measurements recorded by the OCT test device for the at least one eye. In further examples, the instructions of the mobile device are configured to disconnect the mobile device from the OCT test device, and send the received OCT test data from the mobile device to a back office system.

In yet another example, a mobile device includes a display and one or more non-transitory memory configured to store data and instructions. A process can access the memory and execute the instructions stored in the memory. The instructions are programmed to perform a method that includes:

connecting the mobile device with a remote optical coherence tomography (OCT) test system through a wireless link;

providing a graphical user interface on the display, the graphical user interface including a graphical control element;

sending activation instructions through the wireless link to the OCT test device responsive to a user selection of the graphical control element to control the OCT test device to scan at least one eye and record OCT measurements of the at least one eye;

receiving OCT test data from the OCT test device through the wireless link, the OCT test data representing an OCT image of the at least one eye corresponding to the OCT measurements recorded by the OCT test device for the at least one eye;

storing the received OCT test data in the memory;

disconnecting the mobile device from the OCT test device; and sending the received OCT test data from the mobile device to a remote system.

DETAILED DESCRIPTION

This disclosure relates to optical coherence tomography (OCT) systems, devices and methods for monitoring and testing of retinal diseases. Examples of retinal diseases that may be evaluated using systems, devices and methods disclosed herein include macular degeneration (e.g., age-related macular degeneration (AMD)), progressive retinal diseases (e.g., cataracts, diabetic macular edema (DME), and diabetic retinopathy (DR), glaucoma and the like), post surgical retinal conditions (e.g., epiretinal membrane treatment, retinal detachment, macular hole grafts and the like) as well as other macular/fungus pathology monitoring.

In an example, a retinal disease testing system includes an OCT device and a mobile device. The OCT device has an eyepiece that can be coupled to adjustable stand to facilitate positioning the eyepiece in proper alignment with a patient's eye. The OCT device includes one or more OCT probes on a motor configured to automatically focus scans through the eyepiece in response to being activated (e.g., by the patient or other person using user-friendly controls). A control device is coupled to OCT device through an interface. In an example, the interface is a wireless interface. The control device is configured to control the interface and the OCT device to record OCT image data for one or both eyes, which is stored in memory, according to one or more OCT scans implemented by the OCT device.

The mobile device includes a wireless communications interface, a display, and non-transitory memory that includes data and machine-readable instructions (e.g., computer code) that is executable by a processor of the mobile device to perform functions disclosed herein. The instructions can be implemented by the mobile device as an application (e.g., an OCT client application or app) to control the retinal disease testing system, including the OCT device, through the wireless interface. For example, the instructions include a graphical user interface (GUI), such as providing one or more graphical control elements (e.g., scroll bars, buttons, drop-down menus, etc.) on a touch screen display of the mobile device to interact with and/or control the retinal disease testing system.

As an example, the instructions are programmed to connect the wireless interface of the mobile device with the wireless interface of the testing system through a wireless communications link. The GUI on the mobile device can provide a graphical control element (e.g., a trigger region or button) to submit activation instructions, which are sent from the mobile device through the wireless link to the control device of the OCT test system responsive to a user selection of the graphical control element. The control device of the testing system is configured to control the OCT test device to record OCT measurements of one or more eyes responsive to the activation instructions and generate corresponding OCT test data. The OCT test data can represent the OCT measurements recorded by the OCT test device for one or more eyes of a given patient. The application on the mobile device also is programmed receive the OCT test data through the wireless link and store the received OCT test data in the memory of the mobile device. After the test is complete and the OCT test data has been transferred to the mobile device, the instructions can disconnect the mobile device from the OCT test device. Additionally, the OCT test device can delete the OCT test data from its memory, such in response to instructions sent from the mobile device prior to disconnecting or in response to transferring the OCT test data to the mobile device.

The mobile device further can be programmed to send the received OCT test data from the mobile device to a remote system (e.g., a back office system) through a wireless link (e.g., Wi-Fi or cellular data communications link). The remote system can route the images to the patient's ophthalmologist, a local reading center or other healthcare provider. The mobile device can also be configured to directly or indirectly store a copy of the OCT test data in an electronic health record (EHR) for the patient and/or in a private server of the patient's health care provider (e.g., an ophthalmologist). The patient's ophthalmologist (or other health care provider) can then determine if there have been any retinal changes and when treatment or an appointment is actually needed based on a review the OCT image, which may involve a comparison with one or more prior OCT images obtained for the patient. Additionally, or alternatively, artificial intelligence, such as machine learning models, can be used to perform image processing, such as may include enhancing image resolution of the OCT images and/or classifying a state of the eye(s) based on the acquired OCT image data.

The systems and methods disclosed herein enable the patient to be monitored without having to make an appointment or commute to a hospital. For example, patients could access the OCT system at a local establishment, such as a regular eye clinic, pharmacy, grocery store or in their own home. The systems, devices and methods thus enable patients to monitor their retinal health in a convenient setting using their own personal mobile device and without requiring a trained technician or ophthalmologist to be present.

FIG. 1 is a block diagram of an example system 10 for monitoring retinal diseases. The system 10 includes an OCT device 12, a mobile device 14 and a remote system 16. The OCT device 12 includes an OCT spectrometer and associated electronics configured to control an OCT scanner having optical components (e.g., lenses and tubes, grating, mounts and mirrors), a reference arm arranged to scan one or more patient's eyes, schematically shown at 20, and acquire OCT images of the eye.

In the example of FIG. 1, the OCT device 12 is coupled to a control device 22 that is configured to control operation of the OCT device and communication of instructions and data to and/or from the OCT device. In some examples, the control device 22 or a portion thereof could be implemented as part of the OCT device 12 and/or within a common housing with the OCT device. The OCT device 12 and the control device 22 can be coupled together in the form a retinal disease test system (e.g., also referred to herein as an OCT test system) 25, which may be provided as an integrated test system at a respective test location. The control device 22 includes electronics (e.g., hardware and software), including a wireless interface 24 and an OCT driver. For example, the wireless interface 24 is implemented as a wireless network control device configured to communicate data through a wireless communications link such as a Wi-Fi, Bluetooth or a cellular data link. As a further example, the wireless interface 24 is configured to implement a wireless network to enable a secure connection over a wireless link 36 between the control device 22 and the mobile device 14. The wireless interface 24 can implement a peer-to-peer or another connection (e.g., infrastructure-based connection) configured to use security protocols for setup of and access to the wireless communications link.

The control device 22 is programmed (e.g., including an OCT driver) to control the OCT device 12 to record OCT images and store the OCT images as OCT image data in memory, such as may be part of the OCT device 12 and/or the control device 22. The control device 22 is also configured to control the wireless interface to communicate data and instructions over a wireless link 26 between the mobile device 14 and the control device 22. As mentioned, the control device 22 and/or the wireless interface 24 thereof may be implemented within the OCT device 12 to provide the test system 25, such that the wireless link can be between the mobile device 14 and test system 25.

The OCT device 12 is located within a housing that can include one or more eye pieces and mechanical guides arranged to help align a patient's eye (or eyes) 20 with the eye piece to enable scanning of the patient's retina by the OCT device 12. For example, the OCT device 12 and the control device can share at least a portion of a common housing or be otherwise physically integrated together. A number of such test systems 25 can be located at a variety of convenient locations to enable a number of respective patients to obtain OCT scans without having to make appointments or travel to an advanced health care facility, such as a hospital or retinal clinic.

The mobile device 14 includes a display 26, non-transitory memory 28 and one or more wireless interfaces 30. The mobile device 14 may be a smart phone or another device, such as a tablet or laptop computer, which may belong to the user or mounted to a table or other structure where the OCT device 12 is mounted. In an example, the display 26 is implemented as a touch screen interface, which the patient or other user can use to input instructions or commands for controlling the OCT device 12 and the mobile device 14, as disclosed herein. The mobile device 14 can include another user interface (e.g., key pad and/or other buttons) that can be used to input instructions and commands. The non-transitory memory 28 is configured to store data 32 and instructions 34, and a processor (not shown) is configured to access the memory and execute the instructions stored in the memory.

As mentioned, the mobile device 14 also includes one or more wireless interfaces 30, each configured to communicate over a respective wireless network. For example, the instructions 34 are configured to establish a wireless communications link 36 between a respective wireless interface 30 of the mobile device 14 and the wireless interface 24 of the OCT device 12. This can be done native operating system and controls of the mobile device. The wireless interfaces 24 and 30 can be configured to implement the link 36 according to a respective wireless communications technology (e.g., one of the 802.11x standards, Bluetooth, cellular data or other wireless communications technology). The wireless interfaces 24 and 30 can implement an agreed upon security protocol (e.g., encryption, such as Wi-Fi Protected Access (WPA) or WPA2) to encrypt data communicated over the link 36.

The mobile device 14 can provide a graphical user interface (GUI) on the display 26, which includes one or more graphical control element (e.g., a GUI trigger or button). The mobile device 14 sends activation instructions through the wireless link 36 to the control device 22 of the OCT device 12 responsive to a user selection of the graphical control element to provide OCT control instructions. The control device 22 is configured to control the OCT test device to scan at least one eye and record OCT measurements of the at least one eye 20 based on the OCT control instructions. In response, the OCT device 12 is configured to record OCT measurements of the eye 20 and generate corresponding OCT test data, which represents the OCT measurements recorded by the OCT test device for the eye 20.

The OCT device 12 may provide feedback through the wireless link 36 to the instructions (e.g., an OCT client app) running on the mobile device 14 to indicate that scan has been triggered. After one or more OCT images have been acquired for one eye, the OCT device 12 may also provide feedback to indicate that the scan of the respective eye has completed. The OCT device 12 can also be configured to perform an OCT scan to record OCT measurements for the other eye of the patient. The OCT device 12 may be configured automatically move the scanner or eye piece (e.g., along a scanning rail) to enable the test device to scan the other eye. Alternatively, the adjustment to the OCT device 12 may be manually effected by the patient moving their head to place the other eye in line with the eye piece. In another alternative, the scan assembly, including the eye piece of the test device, can be moved manually by the user or other person (e.g., by a lever). The OCT test data for one or both eyes may be stored in local memory of the OCT device 12 or control device 22.

An image quality metric can be computed for the OCT image. The quality metric can be determined, by program code executed by the OCT device 12, the control device 22, the mobile device 14 or the remote system 16. In an example, the quality metric may be determined by the control device 22, in which the feedback is provided over the wireless link 36 between the wireless interface 24 of the OCT device and the wireless interface 30 of the mobile device 14. For example, control device 22 is programmed to determine the quality metric as a binary metric that indicates whether or not a quality of the OCT image (e.g., a series of scans) is acceptable. The OCT image can be generated as a volume scan (e.g., a series of B scans), and the quality analysis is implemented on the batch and, if there are enough images of sufficient quality, the scan as a whole is considered acceptable. The quality of respective scans can be measured based on a total intensity of the OCT image, a signal-to-noise ratio (SNR) of the OCT image and/or based on a quantification of other information contained in image data.

In some examples, the instructions 34 are programmed to provide additional feedback to specify an indication of OCT image quality, such as can be determined by the control device. The feedback thus can be presented on the display 26 to either indicate that the scan was "successful," that is, of high enough quality for clinical use, or that the scan needs to be retaken. The scan is complete when indicated by a light (e.g., illuminated by the control device) and/or another indication provided on the mobile device to specify a fixation point for turning OCT device 12. For example, if the user sees a green or other positive confirmation (visual and/or audible) presented by the mobile device 14, which indicates a successful scan and the user may leave the device. If the user sees or receives another indication that the scan was incomplete/unsuccessful, which indicates a need to redo the OCT scan, the user is instructed to repeat the process of taking another scan as described herein.

After the test is complete, the OCT device 12 is configured to send the OCT test data from the OCT test device to the control device 22 and from the control device through the wireless link 36 to the mobile device 14. The OCT test data can be sent using a secure data communication, such as Hypertext Transfer Protocol Secure) or another secure data communication method (e.g., secure copy protocol). In an example, the control device 22 is configured to access (e.g., retrieve or receive) the OCT test data and send the data to the mobile device 14 via the wireless link 36. The data may be sent after scanning has been completed for each eye, or data for both eyes may be sent via the link 36 together after scans have been completed for both eyes.

After successful transfer of the OCT test data to the mobile device 14, the local OCT test data may be deleted from the memory (e.g., solid state or other memory device) of the OCT test device 12. For example, the OCT device 12 or control device 22, which may be part of the OCT device, is configured to delete the OCT test data from the memory in response to completing the data transfer to the mobile device 14. In this way, the OCT device 12 is not required to include memory to store multiple data sets for one or more patients. Additionally, because the data is not stored, no patient healthcare data remains on the OCT device 12 or control device 22. The deletion of the OCT test data may be invoked by the OCT device 12 (or control device 220 in response to determining that the data transfer has been completed and/or in response to instructions from the mobile device. Alternatively, or additionally, the OCT test data can be deleted in response to a timeout occurring.

The mobile device 14 thus receives the OCT test data through the wireless link 36, and the mobile device is configured to store the received OCT test data in the memory 28, such as part of the data 32. Following or responsive to such data transfer, the wireless link 36 can be terminated. For example, the mobile device 14 is configured to control the wireless interface 30 to terminate the wireless link 36 after the OCT test data has been received. The OCT device 12 can include instructions 34 programmed to cause the wireless link 36 to be terminated in response to or after receiving the OCT test data. Alternatively, the OCT device 12 includes instructions 34 programmed terminate the wireless link 36 in response to a user input. In another example, the control device 22 of the test system 25 can be configured to control the wireless interface 24 to terminate the wireless link 36 after the OCT test data has been successfully sent to and/or received by the mobile device according to the data transfer protocol implemented over the link.

As a further example, the instructions 34 are programmed to control the mobile device to send the received OCT test data from the memory 28 to the remote system 16 over another wireless link 38 between the mobile device 14 and the remote system. In an example, the termination of the wireless link 36 between the mobile device 14 and the OCT device 12 may be required (e.g., a necessary condition precedent) before enabling the client application running on mobile device to send of OCT test data to the remote system 16. Additionally, the mobile device 14 can be configured to control sending of the received OCT test data from the mobile device to the remote system 16 in response to respective user input via the GUI. Thus, the system 10 enables the patient or other authorized user (a friend or family member) additional control when and how to send their OCT scans to the remote system 16. For example, a user can control the mobile device 14 to send the OCT data to the remote system 16 while at the facility where the OCT test system resides, at home or another location where the mobile device can connect to a wide area network, such as the Internet.

In an example, the mobile device multiple wireless interfaces 30, and the mobile device is configured to use another wireless interface, which is different from the wireless interface used to implement the wireless link 36, to implement the wireless link 38 between the mobile device to the remote system 16 for sending the OCT test data. Alternatively, the mobile device 14 can be configured to use the same wireless interface to communicate the OCT test data over the link 38 from the mobile device 14 to the remote system 16 as was used to implement the wireless link 36. The wireless link 38 can provide access to a wide area network, such as the Internet, whereas the link 36 is a wireless LAN or direct connection (e.g., using WiFi Direct). Feedback may also be provided on the display 26 to indicate successful transmission of the OCT data to the remote system 16. The OCT image data can be deleted from the mobile device 14 after successful transmission of the OCT test data to the remote system 16. In other examples, OCT test data from one or more other previous tests may also be stored in the memory of the mobile device 14, such as local memory 28 or remote (e.g., cloud) memory to ensure redundancy in the event of data corruption/loss.

The remote system 16 is configured to store OCT test data for any number of patients, which may utilize any number of respective mobile devices and test systems 25. The remote system 16 can route the images to the patient's ophthalmologist or other healthcare provider as well as place a copy of the OCT data in an electronic health record for the patient. In an example, the OCT test data can be stored as a digital imaging and communications in medicine (DICOM) image file or according to another image format. The patient's ophthalmologist (or other health care provider) can then review and analyze the OCT test data remotely to determine if there have been any retinal changes. The provider can also use the OCT test data to determine when treatment or an appointment is actually needed based on a review the OCT image provided in the OCT test data, which may involve a comparison with one or more prior OCT images obtained for the patient. The OCT images can be obtained at different times using an OCT test system 10 at the same location (e.g., a nearby pharmacy, eye clinic, grocery store, etc.) or patients can use OCT test systems located at a different locations.

In some examples, the remote system 16 can include a machine learning system programmed to analyze OCT test data based on a machine learning model trained based on known (e.g., previously classified) OCT image data sets. In an example, the remote system 16 can implement a machine learning or deep learning model that can be fed lower-resolution input images (corresponding to the OCT image data) and be configured to draw conclusions based on a higher-resolution classified training set. In another example, a machine learning model is programmed to increase resolution of an OCT image by adding pixels to improve quality of the OCT image based on trained high-quality training data. Additionally or alternatively, a machine learning model is trained to provide results data to classify the OCT measurements for the at least one eye. In an example, the machine learning model can provide a binary classification, such as to identify the OCT image as normal (e.g., healthy) or abnormal (e.g., unhealthy). In another example, the machine learning model can be trained identify one of a plurality of features in the OCT image and/or provide a respective diagnosis. In either case, feedback can be sent to a user, such as to the mobile device to provide feedback on the graphical user interface based on the results data.

In some examples, a time stamp is assigned to OCT test data to specify a time of the OCT scan of each eye. Additional information, such as to specify which eye, location of the OCT device and the like may also be added to the OCT test data. The mobile device further may be programmed to store a scan history data in memory of the mobile device. For example, the scan history data includes time information derived from the time stamp for each OCT scan performed for a respective patient. The system further may be implemented to generate a notification based on the time stamp to remind the respective patient when to obtain a next OCT scan. For example, the notification may be a push notification, an email, a calendar entry, a text or phone call to inform the patient when a next scan is needed. This may involve more than one notification provided at different times to help ensure that the patient obtains a next scan at a scheduled time. The instructions 34 on the mobile device 14 may be configured to manage the notifications to the patient.

Figure 2:
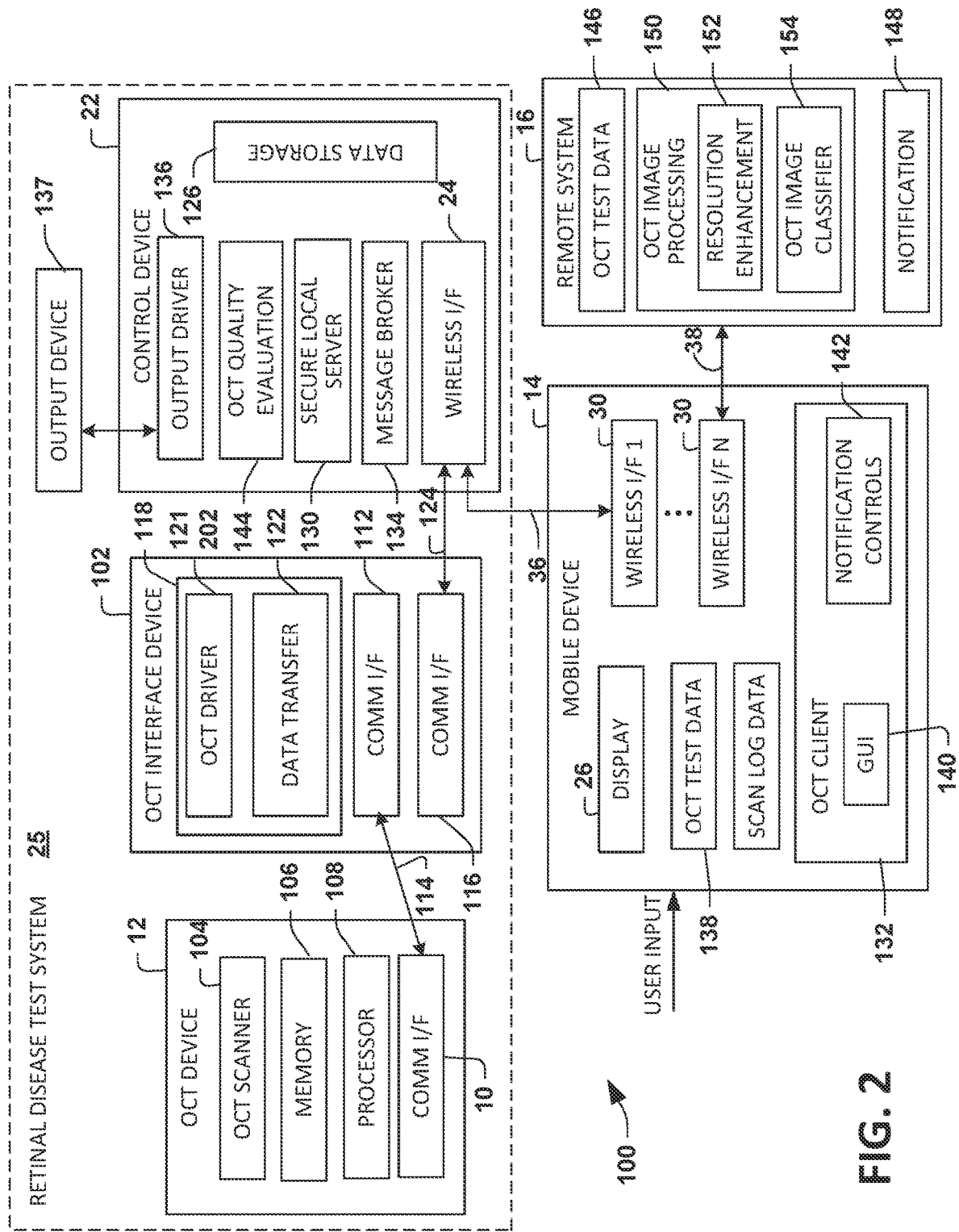
FIG. 2 is a block diagram of another example retinal disease monitoring system.

FIG. 2 depicts an example of another system 100 for monitoring retinal diseases. The system 100 includes parts and features in common with the system 10 of FIG. 1. Accordingly, for sake of consistency, the description of FIG. 2 also refers to FIG. 1. The system 100 includes a retinal disease test system 25. The retinal disease test system 25 can be implemented as a modular architecture, which includes an OCT device 12, an OCT interface 102 and a control device 22. Such an architecture facilitates placing instances of the system 25 at a variety of non-traditional eye care locations, such as grocery stores, pharmacies, clinics or the like. As a result, patients can obtain scans conveniently and more frequently without requiring scheduling and traveling to a hospital or an equipped retinal clinic. For example, a patient can use his or her own mobile device 14 to establish a wireless communications link 36 between the retinal disease test system 25 (e.g., with the control device 22 thereof) for performing OCT scans of one or both eyes. In some examples, prior to initiating a scan, the height and angle of the eyepiece of the OCT device 12 can be manually adjusted by respective user.

The OCT device 12 includes an OCT scanner 104, memory 106, a processor 108 and a communications interface 110. Examples of OCT devices and scanners that can be used are available commercially from Leica Microsystems (e.g., the Leica Envisu C2300) and Lumedica of Durham, N.C., as well as other point-of-care diagnostic, handheld OCT scanners. The OCT scanner 104 includes an OCT probe, a spectrometer and optical components (e.g., lenses and tubes, grating, mounts and mirrors) configured and arranged to scan one or more patient's eyes. The processor 108 is configured to access the memory 106 and execute instructions for controlling the hardware for performing an OCT scan to acquire one or more OCT images of a patient's eye, which can be stored in the memory 106 as OCT test data.

As shown in the example of FIG. 2, the communications interface 110 is coupled to a corresponding communications interface 112 of the interface 110 of the OCT interface device 102 by a wireless communications link 114. Alternatively, the OCT device 12 can include the OCT interface device 102 (e.g., devices 12 and 12 are an integrated device). For example, the link 114 can be a physical link, such as includes one or more electrically conductive links configured to communicate data according to a universal serial bus (USB) or other communications standard (e.g., IEEE 1394, Ethernet, Thunderbolt or the like).

The OCT interface device 102 also includes a wireless interface 116 and a processor 118, which is configured to execute instructions corresponding to interface functions. In the example of FIG. 2 the interface functions include an OCT driver 120 and a data transfer agent 122. The processor 118 is also configured to control the wireless interface 116 as well as to set up and manage communication of data through a wireless communications link 124 between the OCT interface device 102 and the control device 22.

As an example, the wireless interface 116 is configured to receive data and instructions from the control device 22 via the link 124. The data and instructions sent over the link 124 can be encrypted, such as using transport layer security, and the data transfer agent 122 can employ certificates or encryption keys, as needed, to decrypt the incoming data and instructions. For example, the instructions received via the link 124 from the control device 22 (as issued by the mobile device 14, such as in response to a user input) can include a command to invoke a routine in OCT driver to control the OCT device 12 to start a scan and acquire OCT image data. The OCT driver 120 thus can issue corresponding commands to the OCT scanner 104 through the communications link 114. The acquired OCT data, which includes OCT image scans across a patient's eye and time stamp data, can be stored in the memory 106 during the scan process. The OCT data further can be returned to the OCT driver 120 in response to the issued commands. The driver 120 can in turn use the data transfer agent 122 to send the OCT data via the wireless link 124 to the control device. For example, the data transfer agent 122 can be implemented as a background process configured to write received OCT data to data storage 126 of the control device 22, such using a secure file transfer protocol over the link 124 (e.g., an established secure communications channel). As described herein, the data storage 126 can be a temporary data store for the OCT test data, and thus may be deleted after being transferred to the mobile device 14.

In the example of FIG. 2, the control device 22 includes a wireless interface 24, which can include one or more wireless network interface controllers configured to communicate using a respective wireless technologies (e.g., Wi-Fi, Bluetooth, or a cellular data). The wireless interface 24 can be configured to host a wireless network infrastructure that is coupled to the wireless interface 116 as well as allows other devices (e.g., the mobile device 14) to connect to the control device 22 through a wireless link, shown as 36. In an example, each of the wireless links 124 and 36 is implemented as a peer-to-peer wireless connection, such as according to the Wi-Fi direct standard. Other types of connections can be used in other examples. The control device 22 can configured to implement links 124 and 36 concurrently.

As a further example, the control device 22 includes a secure local server (e.g., a web server) 130 configured to handle requests received from the mobile device 14 as well as to manage communication of OCT test data that is generated responsive to a given scan request. For example, the server 130 can be implemented as a web server having a static address (e.g., IP address). The mobile device 14 is programmed to execute application, shown as an OCT client 132, which can employ the IP address of the web server 130 to issue a request for performing an OCT scan through an application programming interface (API). The server 130 thus can receive the scan request and send corresponding instructions through the link 124 to control the OCT interface device 102. For example, the server 130 includes a message broker 134 configured to transport messages and data between the control device and each of the OCT interface 102 and the mobile device 14. In an example, the message broker 134 is implemented as a messaging queuing telemetry transport (MQTT) broker to permit bi-directional communication of messages and data between the OCT device 12 and the mobile device 14. For example, the message broker 134 implements a publication-subscriber architecture, in which the message broker publishes messages by storing them in the data storage for the OCT client 132 via the server 130. The OCT client 132 can both subscribe to receive the messages published by the message broker 134 and publish its scan requests or other commands via the message broker 134. The message broker 134 can utilize transport layer security or other encryption technologies to protect the messages and data being published for the OCT client 132. In an example, responsive to a scan request from the OCT client 132 to the server 130, the message broker 134 can issue a scan command to invoke the scan routine in the OCT driver 120 and control the OCT device 12 accordingly.

The message broker 134 can also be programmed to return received scan status information to the web server 130. The OCT client can poll the web server to receive scan status and related scan information for presentation on the display 26. Additionally, or alternatively, the control device 22 can include an output driver 136 coupled to an output device 137. The output driver 136 can be configured to control the output device to present an indication of the status information, which can include a visual and/or audible presentation. For example, the output device 137 can include a set of one or more light emitting diodes configured to illuminate a respective color LED based on the current status information. For example, the output driver 136 can illuminate a red LED to indicate an error condition and a green LED can indicate completion of a successful scan. In other examples, the output device 137 may be implemented as a display screen to provide a visual representation of received status.

The message broker 134 can also be programmed to receive the OCT test data from the memory 106 of the OCT device 12. For example, the data transfer agent 122 can read the OCT data from the memory 106 and write the OCT data to the data storage 126, such as by the message broker 134 receiving the OCT data via a secure file transfer protocol and storing the data in the data storage 126. The OCT client 132 can receive the OCT test data from the data storage 126 and store it in memory, shown as OCT test data 138.

The OCT client 132 also includes a GUI 140 that includes one or more graphical control elements (e.g., buttons, drop-down menus, radio buttons, user-entry text fields) to receive user input data related to the patient and/or instructions for controlling the OCT scan process. For example, the client 132 can provide a graphical control element (e.g., a button) on the display, which can be activated to start a given scan in response to a user input. Additionally, the client 132 can provide one or more graphical control elements (e.g., a buttons) on the display to select which eye (left or right eye) is to be scanned in response to a user activating the graphical control element.

The OCT client 132 can also include one or more notification controls 142 configured to present status information or other notices on the display 26. For example, the notification controls 142 can provide current status about one or more connections of the mobile device 14, such as including a connection with the retinal disease test system 25 (e.g., via link 36), the wireless link 124 and/or the connection with the remote system 16 (e.g., via link 38). The connection status information can specify whether the connection exists or not and the quality of the connection. As another example, the notification controls 142 can be programmed to provide status information about with a scan being performed by the OCT device 12, such as based on a status message published by message broker 134 to which the client 132 subscribes. Such scan status information may include an indication that the OCT device is ready to scan, a scan is in progress, an error has occurred or a scan has completed. Other status information and notifications may be provided in other examples.

As a further example, the control device can also include an OCT quality evaluation function 144, such as may include instructions executed by the processor of the control device directly and/or by an API to access the function implemented remotely (e.g., in the remote system 16 or another remote location, such as the control device). In an example, the quality evaluation function 144 can compute a quality metric based on the information contained in the OCT image (e.g., as OCT test data in the data storage 126) provided by the OCT device for a given scan. The quality metric can be determined based on image quantification (image content) contained in OCT image. For example, the quality evaluation function 144 is programmed to quantify information in the respective OCT image by summing the intensity value of each pixel in the image to determine a value of total image intensity. For example, if the eye is not positioned properly relative to the eye piece of the OCT device, the size or intensity values in the resulting OCT image will be below a threshold size (e.g., less than a predetermined number of bytes). Additionally, or alternatively, the OCT quality evaluation function 144 can determine whether the quality is acceptable for further analysis based on a signal-to-noise ratio (SNR) of the OCT image. If the OCT quality evaluation function 144 determines that the image is of sufficient quality (e.g., a minimum threshold), the control device 22 can be programmed to provide the OCT image data 138 to the mobile device 14. Alternatively, if the OCT quality evaluation function 144 determines that the image quality is not sufficient quality, the control device 22 can be programmed to provide a message to the mobile device 14 to notify the patient that a scan (or scans need to be repeated). In other examples, the OCT quality evaluation function 144 can be implemented as program code running in the OCT device 12 or mobile device 14.

As described herein, the mobile device 14 also includes a plurality of wireless interfaces 30, shown as wireless interface 1 through N, where N is a positive integer denoting the number of wireless interfaces implemented by the mobile device. In an example, the wireless interfaces 30 can implement different wireless technologies, such as including Wi-Fi, Bluetooth and cellular data. For example, one interface 30 is coupled to the interface 24 via a first link 36 and another interface 30 is coupled to the remote system via another link 38. In another example, the same interface 30 (e.g., Wi-Fi interface) can be used to implement both links 36 and 38 In another example, the OCT client 132 can be programmed to control the wireless interfaces to permit only one of the communication links 36 or 38 to exist at given time, such as described herein. The particular link 36 and/or 38 that is active can be selected by the user, such as using the GUI or native wireless network settings functions of the mobile device 14. The notification controls 142 can further be programmed to present one or more graphical features on the display 26 to indicate each link communication link 36 and/or 38 that is currently active for the mobile device 14.

In an example, the OCT client 132 on the mobile device 14 can use "https POST" (or other request) to send the OCT test data to a web service that stores the OCT image data in a remote file system or data repository. In another example, the OCT client can send (e.g., using "https POST") the OCT data to the remote system 16, which can be implemented as a web service with integrations to an EHR system. In a further example, the OCT test data 138 that is stored in memory of the mobile device 14 can be deleted from the mobile device after the OCT test data has been transferred to the remote system 16.

The remote system 16 can include one or more repository (e.g., a database) to store OCT test data, shown as 146. As described herein, the OCT test data 138, 146 for a given patient can include an OCT image (e.g., multiple A-scans or B-scans) as well as related information including patient data (e.g., name or other patient ID), date and time when the scan was taken, a location identifier where scan occurred, and the like. The OCT image can be stored at 146 as a DiCOM image or other standard or proprietary image format (e.g., JPEG, TIFF, BMP or the like), which further can be compressed format (e.g., zip, gzip, tar or the like) to facilitate transport and storage, such as within a picture archiving and communication system (PACS). Additionally, the stored image can be appended with metadata that provides additional information about the data files, the patient and/or OCT test (e.g., OCT scanner type, location, time etc.).

The remote system 16 can also include a notification function 148 programmed to send a notification (e.g., an email, text, instant message or the like) to a health care provider to alert the health care provider of new OCT test data for the patient. In some examples, the notification function 148 can send the OCT test data itself or a link (e.g., a URL or other address) to the data to the health care provider to facilitate accessing the data. This can be done internally within a secure local network or through an EHR system. The remote system 16 can also store a copy of the OCT test data in an EHR for the patient. The patient's ophthalmologist (or other health care provider) can then determine if there have been any retinal changes and when treatment or an appointment is actually needed based on a review the OCT image, which may involve a comparison with one or more prior OCT images obtained for the patient, which can also be stored in the data repository.

The remote system 16 can also include OCT image processing functions 150. In the example of FIG. 2, the image processing functions 150 includes an image resolution enhancement function 152 and an OCT image classifier 154. The image processing functions 150 can also implement other image processing, such as image processing with Hough transforms for shape detection and/or convolutional filters to identify textures or other image features.

For example, resolution enhancement function 152 can be programmed to increase the number of pixels or voxels in the original (low resolution) OCT image, such as according to a multiplying factor (e.g., a factor of 2, 4 or other factor) to produce a higher resolution version of the OCT image that can be stored in the data repository. In an example, the image resolution enhancement function 152 includes a machine learning model, which is trained based on a high-quality and higher resolution image set of OCT image data. The model can be applied to the original OCT image to increase the image resolution of the OCT image with desired image quality. Examples of image resolution enhancement models that can be implemented as the function 152 include or can be derived from the deep learning super sampling (DLSS) from Nvidia Corporation, generative adversarial networks (GANs) or other approach to enhance the image resolution of the OCT scans provided in the OCT data. The health care provider can analyze the enhanced OCT image data that is produced by the image resolution enhancement function 152 for making an informed diagnosis.

In another example, the OCT image classifier 154 can use one or more machine learning models programmed to analyze the OCT image data (e.g., the original OCT image or the enhanced image produced by the function 152) and classify the OCT image that has been sent from the mobile device 14 for a given patient. The OCT image classifier 154 can implement any of a variety of techniques for generating the models, including support vector machines, regression models, self-organized maps, k-nearest neighbor classification or regression, fuzzy logic systems, data fusion processes, boosting and bagging methods, rule-based systems, or artificial neural networks. In one example, the OCT image classifier 154 can be implemented as an encoder/decoder convolutional neural network (CNN) trained on ImageNet to segment the OCT images and perform image segmentation to classify pixels and clusters of pixels. Such image classification can be trained distinguish between and classify the layers of the retina. In a further example, the OCT image classifier 154 can generate a 'thickness vector map' to estimate retinal thickness at a given segment of the imaged retina.

In an example, the OCT image classifier 154 can include one or more machine learning models trained based on known OCT libraries to implement a binary classification, such as to identify the patient's eye (or eyes) as healthy (e.g., normal) or unhealthy (e.g., diseased). Such binary classification may be implemented without requiring feature extraction from the OCT image. In another example, the OCT image classifier 154 can be programmed to diagnose the OCT image by training one or more machine learning models to perform feature extraction to and, based on the extracted features, perform binary classification. In such example, the 'features' extracted wouldn't may not be specifically clinically relevant features, but they nonetheless can be utilized to help identify and distinguish a 'healthy' vs 'unhealthy' scan based on a weighted model that is implemented by the OCT image classifier 154. As a further example, the OCT image processing function 150 can be programmed to compare the current OCT image test data with one or more prior data sets for a given patient, to ascertain whether and, in some examples, an amount of difference between exhibited between the current OCT scans and one or more prior OCT scans. If the difference exceeds a threshold, a notification can be provided to the mobile unit 14 to have the patient schedule an in-person (or virtual) visit with the patient's health care provider.

In yet another example, such as where image resolution enhancement is performed, the OCT image classifier 154 can be trained to classify respective features. Examples of features that the OCT image classifier 154 can extract from OCT images of various layers of the retina include features within one or more of the nerve fiber layer, ganglion cell layer, inner plexiform layer, inner nuclear layer, outer plexiform layer, outer nuclear layer, temporal nerve fiber layer, the choroid, choriocapillaris, retinal pigment epithelium, photoreceptor outer segments, photoreceptor inner segments, and outer limiting membrane. Where multiple models are used by the OCT image classifier 154, the results of one model (e.g., a model having a highest confidence) can be used to classify the OCT image. Alternatively, the classification determined by two or more models can be combined (e.g., OCT image classifier 154 implemented as a prediction head with multiple trained machine learning model backbones) to classify the OCT image.

The training process of the OCT image classifier 154 will vary with its implementation and which models are used, but training generally involves a statistical aggregation of training data into one or more parameters associated with the output classes. Regardless of the specific model or models that are used employed, the notification function 148 can be programmed to send the classification generated by the OCT image classifier 154 to one or more recipients. For example, the recipients can include the OCT client 132 at the mobile device 14, the patient via another messaging modality (e.g., email, text message, instant message, real-time messaging within private network, EHR notification), the patient's health care provider and/or stored in an EHR for the patient. In an example, the classification can be presented on the user display and acknowledged by the user in response to a user input via the GUI 140.

Figure 3:
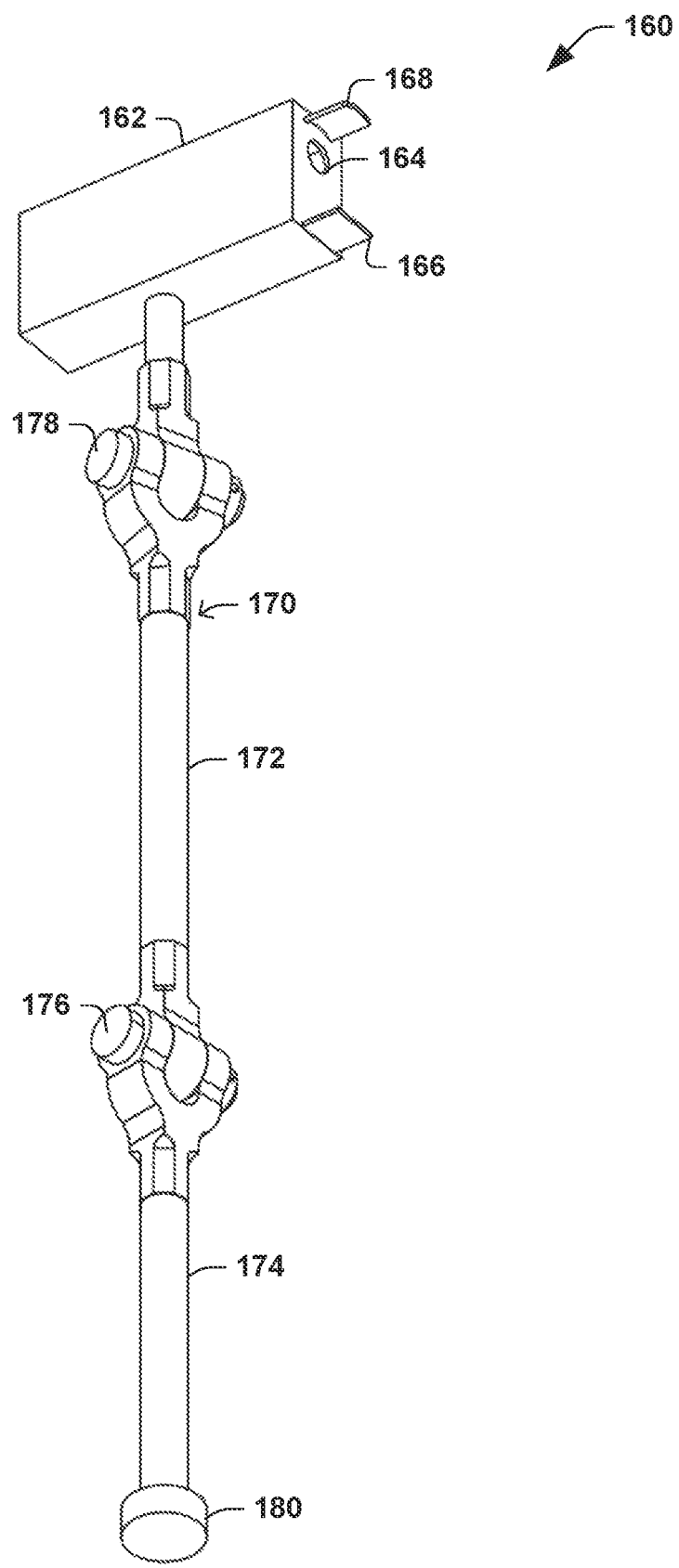
FIG. 3 depicts an example of an OCT apparatus.

FIG. 3 depicts an example of an OCT assembly 160 that includes a housing 162 configured and arranged to house the hardware and software components that form the OCT device 12, such as shown in FIGS. 1 and 2. The housing 162 includes an eye unit 164 on a front surface of the housing. Guides 166 and 168 are also provided on the front surface to help orient a patient's chin and top of the head to facilitate aligning the patient's eye with the eye unit 164. A support bracket 170 extends from the housing to support the housing at a desired position above a base box (not shown). For example, the base box can contain the OCT interface device 102 and/or control device 22, such as shown in FIGS. 1 and 2. In the example of FIG. 3, the bracket 170 includes upper and lower arms 172 and 174. The arms 172 and 174 are coupled together by a joint 176, which can permit relative motion between the arms, such as along one or more axes. Another joint 178 is coupled between the upper arm 172 and the housing 162 to enable addition relative movement between the housing and the upper arm (e.g., along one or more axes). An end 180 of the lower arm 174 can be coupled to a base box or other structure by a coupling (not shown) supported by an eye piece support bracket 204 and legs 206 support the bracket above a base box 208, which includes a top cover (e.g., box top) 210. In a further example, the OCT assembly 160 can include a chin rest, as well as one or more optional attachments for users with difficulty stabilizing. The OCT device within the OCT assembly 160 can further be configured to include optics to help ensure eye alignment and orientation. Additional features can be implemented to mitigate excess light in the patient background and reduce glare from light sources behind the user.

Figure 4:
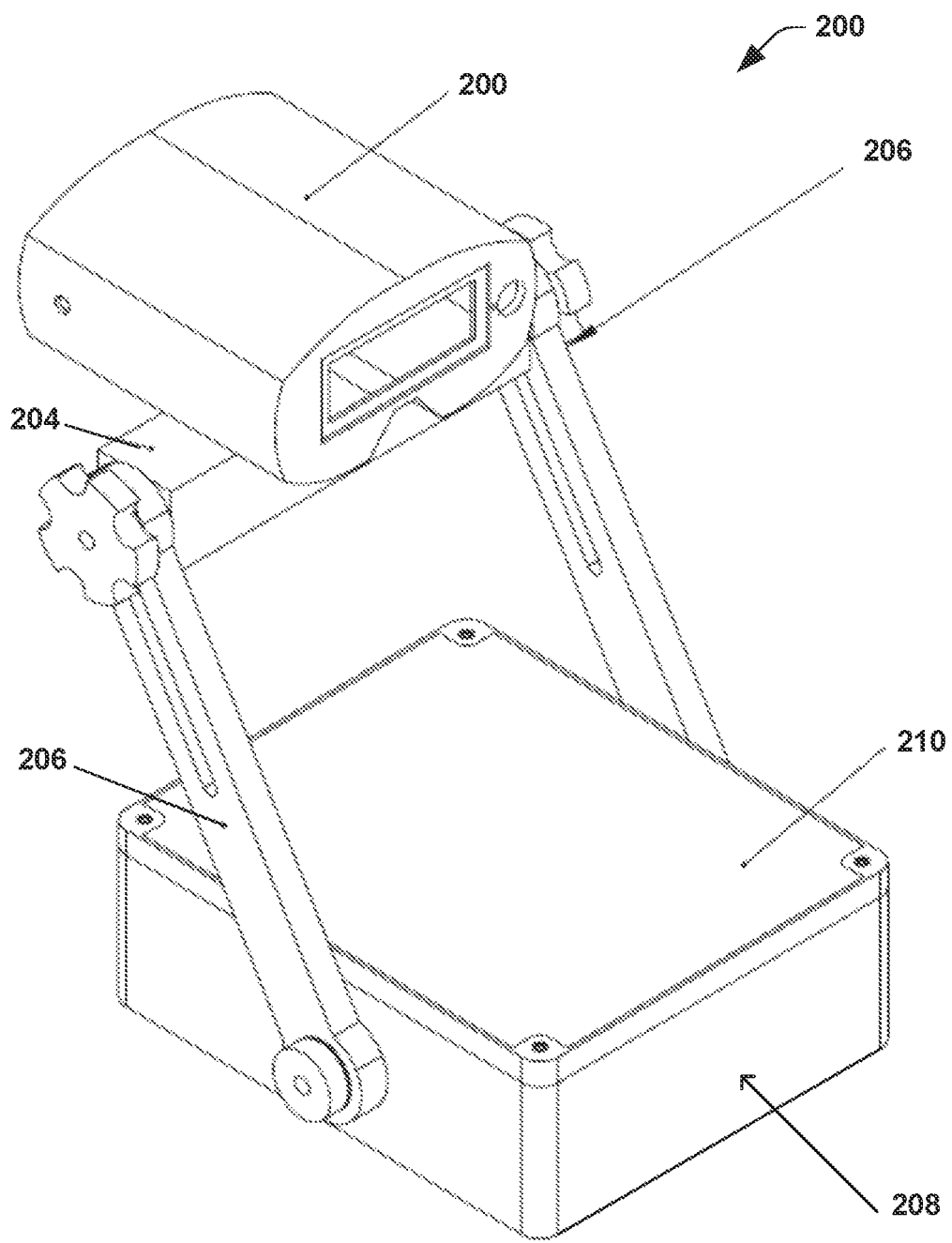
FIG. 4 depicts an example of another OCT apparatus.

FIG. 4 depicts another example of an OCT device 200. The OCT device 200 includes an eye unit 202. The eye unit 202 is supported by a support bracket 204, and one or more legs 206 are configured to support the bracket above a base box 208. The eye unit 202 can contain the hardware (e.g., optical and electronic components) and software of the OCT device 12 (e.g., shown in FIGS. 1 and 2). The base box 208 which includes a top cover (e.g., a box atop) 210. The base box can contain the OCT interface device 102 and/or the control device 22 (e.g., shown in FIGS. 1 and 2).

In an example, the eye unit 202 has a shape of a goggle and has a depth of about 7 inches to ensure an OCT device can be placed inside of the eye piece. The overall shape of the eye unit 202 is designed to accommodate people with different pupillary distances. The front of the eye unit 202 can be assembled with a foam/cushion lining so that patients can lean onto the eye-piece with comfort. The back of the eye unit 202 has a window that can be closed up with screws. It is used for easy access and maintenance of the OCT scanner, which may be implemented within of the eye-piece. The back of the eye unit also has a hole to allow wire bundles to come through.

As a further example, the eye unit 202 is installed onto a sliding rail, while the OCT scanning components within the unit 202 remain fixed (will not move with the head piece). Because, in some examples, the OCT scanning system can only scan one eye at a time, patients will hold the eye unit and move it left and right so that they can scan the other eye (e.g., if the OCT is scanning the patient's right eye first. For example, the patient will move the eye-piece to the left, since the OCT scanner itself is configure to remain stationary and not move along with the eye unit and the OCT scanner will be on the left side of the eye unit and can scan the patient's left eye.

With hinges installed at the sides of the base 208, such as at top and/or bottom ends of the legs 206, the tilting mechanism allows the stage and the eye unit to move towards and away from the patients to accommodate different sitting postures and leaning angles. With the vertical slots on both sides of the legs, the patients can loosen screws and move the eye unit up and down to accommodate different heights. For example, the base 208 is configured as a box with a top 210 that can be screwed to the rest of the box. The box has several holes and removable silicone caps on the sides, which allows cables to come through.

Figure 5:
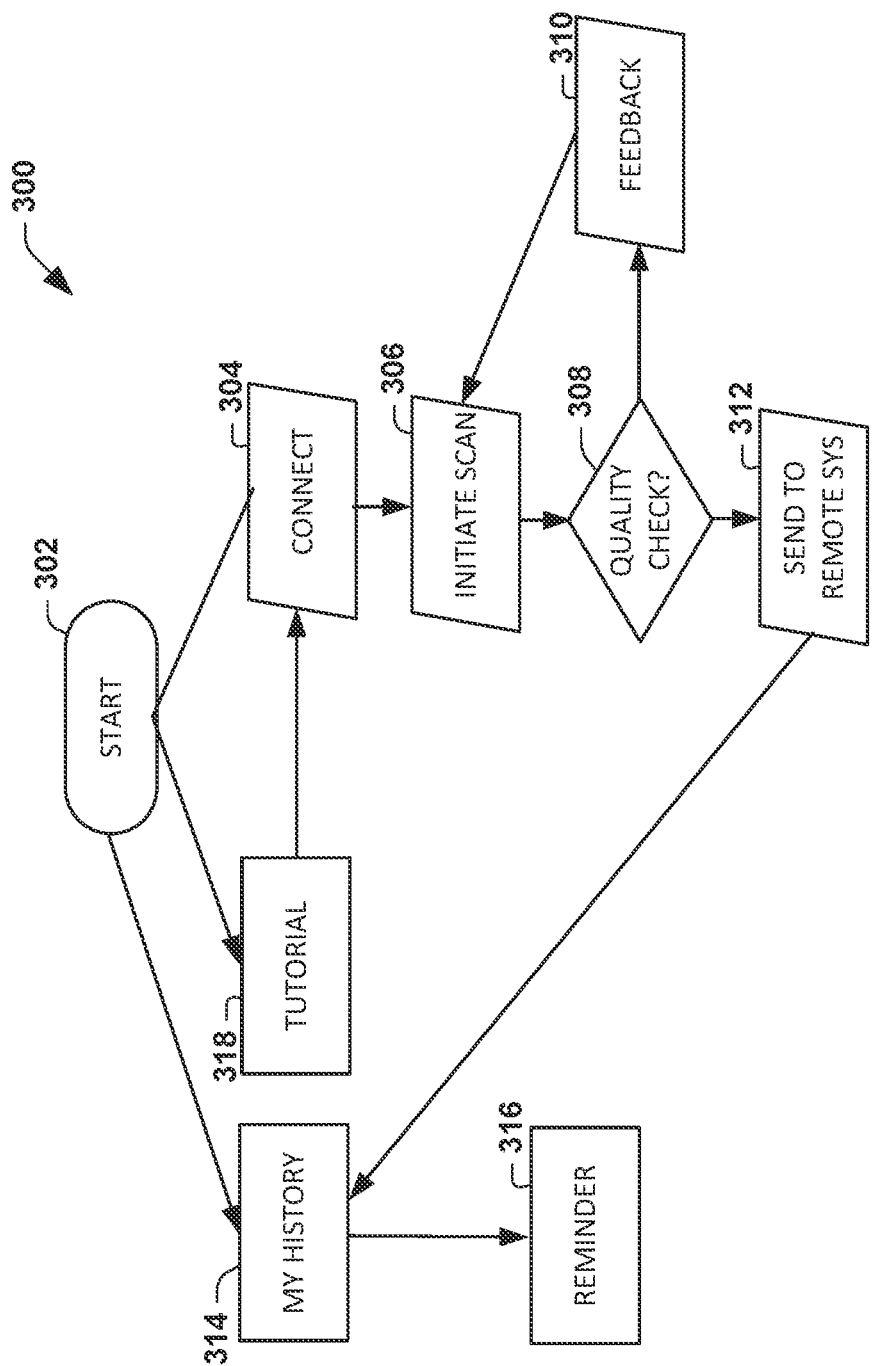
FIG. 5 is a flow diagram depicting an example of software workflow that can be implemented by an OCT client.
Figure 7:
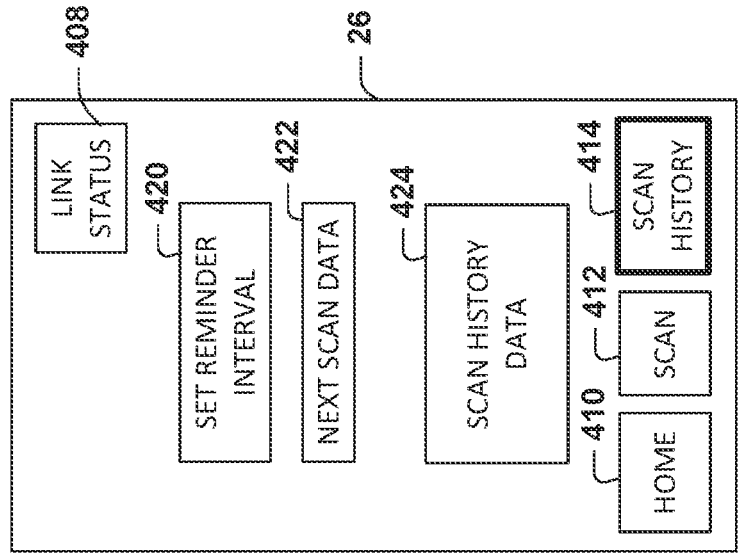
FIG. 7 depicts an example of a scan history display screen that can be generated by an OCT client.
Figure 6:
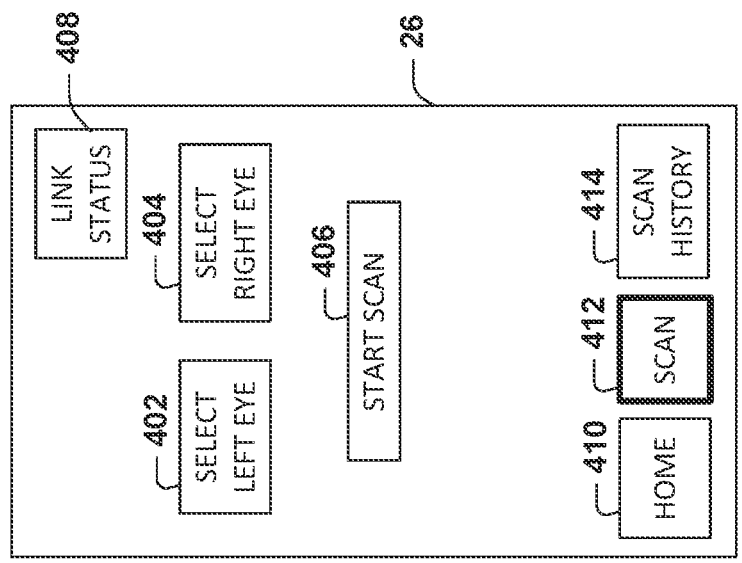
FIG. 6 depicts an example of a scan display screen that can be generated by an OCT client.

FIG. 5 is a flow diagram 300 depicting an example of software workflow for implementing functionality of the system 10, 100, such as described herein, particularly from the perspective of instructions executed by the mobile device 14. Examples of screen shots that may be implemented and presented on the display 26 of the mobile device 14, corresponding to the flow diagram 300, are shown in FIGS. 6 and 7. Accordingly, for sake of clarity the description of FIG. 5 also refers to FIGS. 6 and 7.

In response to opening an OCT client app (e.g., OCT client 132) on the mobile device 14, the OCT client is programmed to present a start screen (e.g., a home screen) on the display 26. As shown in FIG, the start screen includes graphical control elements (e.g., buttons) that can be activated to access other screens associated with the OCT methods disclosed herein. For example, the workflow can proceed to 304, in which the mobile device can connect wirelessly with the retinal disease test system 25 through a wireless link (e.g., wireless link 36). The OCT client can provide detailed instructions (e.g., written or verbal) to help the user connect the mobile device with the system 25. Once connected, the OCT client 132 can present a graphical indication that the mobile device is connected with the system 25 via the wireless link. For example, the link 36 can provide for communication between wireless interfaces 24 and 30 of the control device 22 and the mobile device 14, respectively.

After connecting the mobile device 14 and the test system 25 via link 36, the method 300 can proceed to 306, such as in response to a user input via the GUI 140 to open a scan page. At 306, the mobile device can be activated to initiate an OCT scan, such as in response to a user input via the GUI 140. By way of example, with reference to FIG. 6, the OCT client can provide a GUI on the display (e.g., a touch screen) 26. In the example of FIG. 6, the GUI includes graphical control elements 402 and 404 to select the left or right eye for scanning. After the appropriate eye has been selected, the scan may be started (at 306) in response to a user input activating a start scan graphical control element 406. Once the user activates the scan, there can be a time delay (e.g., default time interval), which can be implemented by the mobile device 14 to delay sending the control instructions to the OCT device 12, to provide time between patient pressing the 'start scan' graphical control element and implementing the actual scan taking place to allow for the patient to orient themselves. Audible and visual indicators can be provided to inform the user of when the scan is about to start and when it is in progress. Also shown in FIG. 6 (as well as FIG. 7), the OCT client can generate can present a link status indicator 408 on the display 26 to specify the status of the wireless link 36. The OCT client can also be programmed to provide a home graphical control element 410, a scan graphical control element 412 and a scan history graphical control element 414. Each of the respective graphical control elements 410, 412 and 414 may be activated in response to a user input to open a respective page (or screen) of the OCT client. The page shown in FIG. 6 depicts an example of a scan page.

After the OCT device completes scan, the OCT image data can be transferred to the mobile device, such as described herein with respect to FIGS. 1 and 2. At 308, the method 300 can include performing a quality check. For example, the OCT quality evaluation function 144 can be programmed to determine whether the acquired OCT image of the selected eye is of sufficient quality or the OCT scan of the selected eye needs to be repeated. If the quality check (at 308) determines that the OCT scan is "bad" and needs to be repeated, the method proceeds to 310 to provide feedback to the user. For example, the notification controls 412 can generate feedback that is presented on the display 26 to specify that the OCT scan needs to be repeated, and the method returns to 306 to initiate another OCT scan. If the quality check (at 308) determines that the OCT scan is "good" the method can proceed to 312 and a routine can be executed by the OCT client to send the acquired OCT data to the remote system 16, such as disclosed herein. From 312, the method proceeds to 314, in which the scan history (e.g., a log of OCT scans) for the patient is updated to include information describing the successfully completed OCT scan. In a further example, the method can include a tutorial 318, such as may be entered from the start screen.

FIG. 7 shows another example of a scan history page and associated graphical control elements that the OCT client can provide on the display 26. In the example of FIG. 7, the GUI includes a set reminder graphical control element 420, which can be used to set the time interval and next OCT scan to be performed, such as in response to a user input. The scan history page can also present a textual and/or graphical visualization 422 specify next scan data (e.g., a date when the next scan should be taken according to the interval specified by graphical control element 420. The scan history page can also include a listing of scan history data, shown at 424, which can display a list describing when each prior scan has been taken. Similar to the scan page shown in FIG. 6 (, the OCT client can generate can present the link status indicator 408 as well as include the home graphical control element 410, scan graphical control element 412 and scan history graphical control element 414 for navigation through the functions of the OCT client.

In further view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, flash memory, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processors of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a,", "an," "a first," or "another" element, or the equivalent thereof, it should be interpreted to include one or more than one such element, neither requiring nor excluding two or more such elements. As used herein, the term "based on" means based at least in part on.

What is claimed is:

1. A method comprising:
    establishing a wireless link between a mobile device and an optical coherence tomography (OCT) test system, which includes a wireless interface;
    executing an application on the mobile device that activates the OCT test system to perform an OCT scan of at least one eye and record OCT measurements for the OCT scan of the at least one eye;

receiving OCT test data at the mobile device from the OCT test system through the wireless link, the OCT test data representing the OCT measurements recorded by the OCT test system for the OCT scan of the at least one eye;

terminating the wireless link, by the application executing on the mobile device, to disconnect the mobile device from the OCT test system;

controlling the mobile device, by the application executing on the mobile device, to send the received OCT test data from the mobile device to a remote system;

receiving results data at the application executing on the mobile device from the remote system, wherein the results data classify a condition of the at least one eye based on a comparison of the OCT test data with training data; and providing feedback on a graphical user interface of the mobile device by the application executing on the mobile device based on the results data.

2. The method of claim 1, further comprising:
comparing at least a portion of the received OCT test data with prior OCT test data stored in memory of the mobile device; and
generating the feedback on the mobile device based on the comparison.

3. The method of claim 1, further comprising:
disabling the sending of the received OCT test data from the mobile device while the mobile device is connected with the OCT test system through the wireless link; and
enabling the sending of the received OCT test data from the mobile device to the remote system in response to detecting the mobile device is disconnected from the OCT test system.

4. The method of claim 3, wherein the sending of the received OCT test data from the mobile device to the remote system is controlled in response to respective user input via the graphical user interface.

5. The method of claim 1, wherein the OCT test data, which is received at the at the mobile device from the OCT test system and sent to the remote system, includes an OCT image of the at least one eye based on the OCT scan of the at least one eye.

6. The method of claim 1, wherein the received OCT test data is sent from the mobile device to the remote system using a wireless interface of the mobile device that is different from a wireless interface of the mobile device used by the mobile device for connecting the mobile device to the OCT test system through the wireless link.

7. The method of claim 1, wherein the wireless link is a first wireless link, wherein the OCT test system includes an OCT scan device and a control device, the OCT scan device being coupled to or including a respective wireless interface, the control device being coupled to the respective wireless interface of the OCT scan device through a second wireless link.

8. The method of claim 7, wherein the control device includes the wireless interface of the OCT test system, and is configured to implement the respective first and second wireless links concurrently.

9. The method of claim 7, further comprising:
storing the OCT test data in memory of the OCT test system; and
deleting the stored OCT test data from memory of the OCT test system after and/or in response to being sent to the mobile device via the second wireless link.

10. The method of claim 1, further comprising assigning a time stamp to OCT test data to specify a time of the OCT scan of the at least one eye.

11. The method of claim 10, further comprising storing a scan history data in memory of the mobile device, the scan history data comprising time information derived from the time stamp for at least a most recent OCT measurement performed for a respective patient.

12. The method of claim 10, generating a notification based on the time stamp to remind the respective patient when to obtain a next OCT scan.

13. The method of claim 1, further comprising:
analyzing, at the remote system, at least a portion of the received OCT test data based on a machine learning model to provide the results data classifying the OCT measurements for the at least one eye; and
generating feedback on the graphical user interface based on the results data.

14. One or more non-transitory media that stores instructions that, when executed by one or more processors, cause the one or more processors to perform the method of claim 1.

15. The method of claim 1, further comprising:
providing a notification at the mobile device to have the patient make an in-person or virtual visit with a healthcare provider based on the results data.

16. A system for monitoring retinal disease, comprising:
a retinal disease testing system comprising:
an optical coherence tomography (OCT) device configured to record OCT image data based on an OCT scan;
a wireless interface; and
a control device configured to control the OCT device and the wireless interface;
a mobile device including a wireless interface, a display, and non-transitory memory that includes instructions configured to at least:
connect the wireless interface of the mobile device with the wireless interface of the testing system through a wireless link;
control the OCT device to perform an OCT scan of at least one eye and record OCT measurements for the OCT scan of the at least one eye;
receive the OCT test data from the retinal disease testing system through the wireless link and store the received OCT test data in the memory of the mobile device, the stored OCT test data representing the OCT measurements recorded by the OCT device for the at least one eye;
disconnect the mobile device from the retinal disease testing system;
send the received OCT test data from the mobile device to a remote system;
receive results from the remote system, wherein the results data classify the OCT measurements based on a comparison of the OCT test data with training data; and
provide feedback on the display of the mobile device based on the results data.

17. The system of claim 16, wherein the wireless interface of the mobile device is a first wireless interface, the mobile device comprising a second wireless interface, the instructions of the mobile device further configured to send the received OCT test data from the mobile device to the remote system using one of the first or second wireless interfaces of the mobile device.

18. The system of claim 16, wherein the wireless link is a first wireless link, and the control device includes the wireless interface of the testing system, wherein the OCT device is coupled to or includes a second wireless interface, the control device being coupled to the second wireless interface of the OCT device through a second wireless link, and wherein the control device is configured as a wireless access point to implement the respective first and second wireless links.

19. The system of claim 18, wherein the OCT device includes local memory, and the OCT device is configured to delete the OCT test data from the memory of the OCT device after and/or in response to the OCT test data being sent to the mobile device via the second wireless link.

20. The system of claim 16, further comprising a machine learning model trained on OCT training test data sets of OCT measurements, each having known classification, the machine learning model programmed to provide results data classifying the OCT measurements for the at least one eye, wherein the mobile device is programmed to provide the feedback on a graphical user interface (GUI) on the display of the mobile device based on the results data.

21. The system of claim 16, wherein the mobile device includes further instructions to provide a notification at the mobile device to have the patient make an in-person or virtual visit with a healthcare provider based on the results data.

22. The system of claim 16, wherein the OCT test data, which is received at the at the mobile device from the retinal disease testing system and sent to the remote system, includes an OCT image of the at least one eye.

23. A mobile device comprising:

a display;

one or more non-transitory memory configured to store data and instructions;

a processor to access the memory and execute the instructions stored in the memory, wherein the instructions are programmed to perform a method comprising:

connecting the mobile device with a remote optical coherence tomography (OCT) test system through a wireless link;

providing a graphical user interface (GUI) on the display, the GUI including a graphical control element;

sending activation instructions through the wireless link to the OCT test system responsive to a user selection of the graphical control element to control the OCT test system to scan at least one eye and record OCT measurements of the at least one eye;

receiving OCT test data from the OCT test system through the wireless link, the OCT test data including an OCT image of the at least one eye corresponding to the OCT measurements recorded by the OCT test system for the at least one eye;

storing the received OCT test data in the memory;

disconnecting the mobile device from the OCT test system; and controlling the mobile device, in response to a user input, to send the OCT test data, including the OCT image, from the mobile device to a remote system;

receiving results data at the mobile device from the remote system, wherein the results data classify a condition of the at least one eye based on a comparison of the OCT test data with training data; and providing feedback on the GUI of the mobile device based on the results data.

\* \* \* \* \*